(12) United States Patent
Navia et al.

(10) Patent No.: US 8,512,403 B2
(45) Date of Patent: Aug. 20, 2013

(54) ANNULOPLASTY RING WITH WING MEMBERS FOR REPAIR OF A CARDIAC VALVE

(75) Inventors: Jose Luis Navia, Shaker Heights, OH (US); Jose Antonio Navia, Buenos Aires (AR); Mark S. Goodin, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 2916 days.

(21) Appl. No.: 10/850,508

(22) Filed: May 20, 2004

(65) Prior Publication Data

US 2004/0243230 A1 Dec. 2, 2004

Related U.S. Application Data

(60) Provisional application No. 60/472,030, filed on May 20, 2003, provisional application No. 60/548,416, filed on Feb. 26, 2004.

(51) Int. Cl.
*A61F 2/24* (2006.01)

(52) U.S. Cl.
USPC ....................................................... 623/2.36

(58) Field of Classification Search
USPC ............... 623/1.11, 1.24, 1.26, 2.11, 2.14, 623/2.36, 2.37, 1.36, 904, 2.17; 606/191, 606/192, 194
See application file for complete search history.

(56) References Cited

U.S. PATENT DOCUMENTS

| | | | |
|---|---|---|---|
| 6,361,556 B1 | 3/2002 | Chuter | |
| 6,406,493 B1 | 6/2002 | Tu et al. | |
| 6,419,696 B1 | 7/2002 | Ortiz et al. | 623/2.37 |
| 6,821,291 B2 * | 11/2004 | Bolea et al. | 623/1.11 |
| 2002/0002401 A1 | 1/2002 | McGuckin, Jr. et al. | 623/1.36 |
| 2003/0040793 A1 | 2/2003 | Marquez | |
| 2003/0109924 A1 | 6/2003 | Cribier | 623/2.18 |
| 2003/0191528 A1 | 10/2003 | Quijano et al. | 623/2.37 |
| 2003/0199974 A1 | 10/2003 | Lee et al. | |
| 2003/0220686 A1 | 11/2003 | Arru et al. | |
| 2004/0039442 A1 | 2/2004 | St. Goar et al. | |
| 2005/0055087 A1 | 3/2005 | Starksen | |

FOREIGN PATENT DOCUMENTS

| | | |
|---|---|---|
| EP | 850607 A1 * | 7/1998 |
| EP | 1 348 406 A1 | 10/2003 |
| WO | WO 0066033 A1 * | 11/2000 |
| WO | WO-03/028558 A2 | 4/2003 |
| WO | WO 03/088875 A1 | 10/2003 |
| WO | WO 03/105730 A1 | 12/2003 |

* cited by examiner

*Primary Examiner* — Brian Pellegrino
(74) *Attorney, Agent, or Firm* — Tarolli, Sundheim, Covell & Tummino LLP (57) ABSTRACT

An annuloplasty ring for repairing a cardiac valve includes an expandable support member having oppositely disposed proximal and distal end portions and a main body portion between the end portions. The proximal end portion of the support member includes a plurality of wing members that extend from the main body portion. Each of the wing members includes at least one hook member for embedding into a cardiac wall and the valve annulus to secure the annuloplasty ring in the valve annulus. The annuloplasty ring may be expanded into full contact engagement with the annulus of the cardiac valve by an inflatable balloon. Methods for repairing a cardiac valve using the annuloplasty ring are also provided.

20 Claims, 6 Drawing Sheets

ANNULOPLASTY RING WITH WING MEMBERS FOR REPAIR OF A CARDIAC VALVE

RELATED APPLICATIONS

This application claims priority from U.S. provisional patent application Ser. No. 60/472,030, filed on May 20, 2003, and U.S. provisional patent application Ser. No. 60/548,416, filed on Feb. 26, 2004. The subject matter of the above-listed provisional patent applications is incorporated herein by reference.

FIELD OF THE INVENTION

The present invention relates to an apparatus and methods for repair of a cardiac valve, and is particularly directed to an apparatus and methods that include an annuloplasty ring for the correction of mitral valve and tricuspid valve disorders.

BACKGROUND OF THE INVENTION

There are two atrio-ventricular valves in the heart; one on the left side of the heart and one on the right side of the heart. The left side atrio-ventricular valve is the mitral valve and the right side atrio-ventricular valve is the tricuspid valve. Both of these valves are subject to damage that requires that the valve be repaired or replaced. Experience has shown that damaged valves can be surgically repaired, and that the long term results obtained from valve repair can be better than replacement of the valve.

The mitral and tricuspid valves differ significantly in anatomy. While the annulus of the mitral valve is generally D-shaped, the annulus of the tricuspid valve is more circular. The effects of the valvular dysfunction vary between the mitral valve and the tricuspid valve. Mitral valve regurgitation has more severe physiological consequences to the patient than does tricuspid valve regurgitation, a small amount of which is tolerable. In patients with valvular insufficiency, it is increasingly common surgical practice to retain the natural valves and to attempt to correct the defect. Many of these defects are associated with dilation of the valve annulus. This dilatation not only prevents competence of the valve, but also results in distortion of the normal shape of the valve orifice. Remodeling the valve annulus is therefore central to most reconstructive procedures for both the mitral and tricuspid valves.

Mitral or tricuspid valve annuloplasty is a restoration of the valve annulus, which effects full closure of the valve's leaflets by reestablishing the size and the shape of the normal mitral or tricuspid valve annulus. Surgical procedures such as annuloplasty more commonly incorporate the use of a prosthetic ring, where the ring is implanted over or within the mitral or tricuspid valve annulus.

In mitral valve insufficiency, the valve leaflets do not fully close and a certain amount of blood leaks back into the left atrium when the left ventricle contracts. As a result, the heart has to work harder by pumping not only the regular volume of the blood, but also the extra volume of blood that regurgitated back into the left atrium. The added workload creates an undue strain on the left ventricle. This strain can eventually wear out of the heart and result in morbidity when the conditions are prolonged and severe enough. Consequently, proper function of the mitral valve is critical to the pumping efficiency of the heart.

Many surgical procedures have been described to correct pathology of the valve leaflets, chordal tendineae, and papillary muscles. In mitral valve repair, it is desirable to preserve the normal distance between the two fibrous trigones. The trigones more or less straddle the anterior leaflet portion of the mitral annulus. A significant surgical reduction of the inter-trigonal distance could cause left ventricular outflow tract obstruction. Thus, it is desirable to maintain the natural inter-trigonal distance after mitral valve surgery. Consequently, when a mitral valve is repaired, the result is generally a reduction in size of the posterior segment of the mitral valve annulus.

In a mitral valve repair, it is necessary to either diminish or constrict the involved segment of the mitral annulus so that the leaflets may coapt correctly when closing or, alternatively, to stabilize the annulus to prevent the possibility of dilatation from occurring. The latter is frequently achieved by implantation of a prosthetic ring in the supra-annular position. The purpose of the ring is to restrict and/or support the annulus to correct and/or prevent valvular insufficiency. However, it is important not to over-restrict the annulus or unacceptable valve stenosis could result.

As described above, in mitral valve repair, constriction of the mitral annulus should take place only in the area of the posterior portion of the native valve annulus. Shortening of the posterior portion of the mitral valve annulus may be accomplished by implanting an inexpansible rigid ring. With this approach, the surgeon must accurately choose the size of the ring that would prevent insufficiency, yet will not cause significant valve stenosis. A second approach uses a contractible ring that may be plicated during implantation. This approach has a disadvantage that a surgeon must accurately gauge not only the ring size to use, but also how to space the implanting sutures in the ring and the native annulus so that, when implanted, insufficiency is minimized. A third approach involves semi-expandable rings that may be contracted only in appropriate segments of the native annulus (but not in the anterior portion). The natural inter-trigonal distance should be maintained and the anterior leaflet should not be diminished in this circumstance.

In tricuspid valve repair, constriction of the annulus usually takes place in the posterior leaflet segment and in a small portion of the adjacent anterior leaflet. The septal leaflet segment is not usually required to be shortened.

Mitral and tricuspid valve disease is traditionally treated by surgical repair with an annuloplasty ring or surgical or replacement with a valve prosthesis. However, surgical valve replacement or repair is often an exacting operation that is done through a surgical technique where the thoracic cavity is opened. The operation requires use of a heart-lung machine for external circulation of the blood as the heart is stopped and opened during the surgical intervention and the artificial cardiac valves and/or annuloplasty rings are sewed in under direct vision. This operation exposes the patient to many risks especially in the elderly population. A percutaneous procedure that can be performed under local anesthesia in the cardiac catherization lab, rather than in cardiac surgery, could therefore offer tremendous benefits for these patients, many of whom have no options today. A minimally invasive surgical technique and percutaneous approach for delivering a prosthetic ring for mitral or tricuspid valve repair could be one of the most prominent tools in order to provide opportunities to treat patients with severe valvular insufficiency and/or end stage heart failure.

SUMMARY OF THE INVENTION

The present invention is an annuloplasty ring for repairing a cardiac valve. The annuloplasty ring comprises an expandable support member having oppositely disposed proximal and distal end portions and a main body portion between the end portions. The proximal end portion of the support member comprises a plurality of wing members that extend from the main body portion. Each of the wing members includes at least one hook member for embedding into a cardiac wall and into the annulus of the cardiac valve to secure the annuloplasty ring in the annulus.

In accordance with one aspect of the invention, the hook members, when embedded into the cardiac wall and the valve annulus, extend distally from the wing members.

In accordance with another aspect of the invention, the main body portion has a concave cross-sectional shape for conforming to the convex shape of the valve annulus.

In accordance with another aspect of the invention, each of the wing members has a concave cross-sectional shape for conforming to the convex shape of the valve annulus.

In accordance with another aspect of the invention, the main body portion and the wing members are resiliently bendable from the concave cross-sectional shapes into flatter cross-sectional shapes for delivery and placement of the annuloplasty ring.

In accordance with another aspect of the invention, the apparatus further comprises a constraining wire for temporarily holding the wing members in the flatter cross-sectional shape. The hook members extend generally radially when the wing members are being held in the flatter cross-sectional shape by the constraining wire.

In accordance with another aspect of the invention, the hook members are resiliently bendable to extend proximally inside a delivery capsule or sleeve during delivery of the annuloplasty ring into the valve annulus.

In accordance with another aspect of the invention, the annuloplasty ring further comprises a layer of biocompatible material covering at least a portion of the distal end portion and the main body portion of the support member.

In accordance with another aspect of the invention, the support member is made from a shape memory material that is responsive to changes in temperature above and below a predetermined temperature transition range. The support member has a first configuration when the temperature is below the predetermined temperature transition range and a second configuration when heated above the predetermined temperature transition range.

In accordance with another aspect of the invention, the annuloplasty ring is insertable into the annulus of the cardiac valve in the first configuration and is thereafter heatable above the predetermined temperature transition range to change the support member into the second configuration, wherein movement of the support member into the second configuration causes a reduction in size of the opening defined by the valve annulus.

In accordance with another aspect of the invention, the support member is expandable by an inflatable balloon so that the annuloplasty ring engages the annulus of the cardiac valve.

The present invention further includes an apparatus for repairing a cardiac valve. The annuloplasty ring comprises an expandable support member having oppositely disposed proximal and distal end portions and a main body portion between the two end portions. The proximal end of the support member includes a plurality of wing members that extend from the main body portion. Each of the wing members includes at least one hook member for embedding into a cardiac wall and the annulus of the cardiac valve to secure the annuloplasty ring in the annulus. An inflatable balloon expands the support member so that the annuloplasty ring engages the annulus of the cardiac valve with full contact.

In accordance with one aspect of the invention, the balloon has an hourglass shape defined by first and second bulb sections connected by a center section having a smaller diameter than the bulb sections. The annuloplasty ring is positioned about the center section.

The present invention further provides a method for repairing a cardiac valve. According to the inventive method, an annuloplasty ring having an expandable support member is provided. The annuloplasty ring is placed around an inflatable balloon in a secured manner. The balloon and annuloplasty ring are then inserted into an atrial chamber and advanced until the annuloplasty ring is positioned within the annulus of the cardiac valve to be repaired. Next, the support member is extended with the balloon so that the annuloplasty ring engages the annulus of the cardiac valve. The annuloplasty ring is secured in the valve annulus. The balloon is then collapsed and removed from the atrial chamber.

In accordance with another aspect of the inventive method, the balloon has an hourglass shape defined by first and second bulb sections connected by a center section having a smaller diameter than the bulb sections. The annuloplasty ring is positioned about the center section.

In accordance with another aspect of the inventive method, a first bulb section of the balloon is positioned within the leaflets of the native valve so that, when the balloon is inflated, the first bulb pushes the valve leaflets back to protect the leaflets during expansion of the support member.

In accordance with another aspect of the inventive method, the support member has oppositely disposed proximal and distal end portions connected by a main body portion that has a concave cross-sectional shape. The step of expanding the support member with the balloon so that the annuloplasty ring engages the annulus of the cardiac valve includes conforming the concave main body portion to the convex shape of the valve annulus to help locate and secure the annuloplasty ring in the valve annulus.

In accordance with another aspect of the inventive method, the proximal end of the support member comprises a plurality of wing members that extend from the main body portion. Each of the wing members includes at least one resiliently bendable hook member extending from each of the wing members. The method further includes the step of embedding the hook members into a cardiac wall to further secure the annuloplasty ring in the valve annulus.

In accordance with another aspect of the inventive method, each of the wing members has a concave cross-sectional shape for conforming to the convex shape of the valve annulus. The method further comprises the step of pulling the wing members into a flatter cross-sectional shape with a constraining wire for placement of the annuloplasty ring. The hook members extend generally radially when the wing members are being held by the constraining wire.

In accordance with another aspect of the inventive method, the hook members are bent to extend proximally inside a delivery capsule or sleeve for delivery of the annuloplasty ring.

In accordance with another aspect of the inventive method, the constraining wire is released after the step of expanding the support member with the balloon so that the wing members bend radially outward to position the hook members above the valve annulus for embedding into the valve annulus.

In accordance with another aspect of the inventive method, the step of releasing the constraining wire causes the hook members to embed into the cardiac wall in the distal direction.

In accordance with another aspect of the inventive method, the support member is made from a shape memory material that is responsive to changes in temperature above and below a predetermined temperature transition range. The support member has a first configuration when the temperature is below the predetermined temperature transition range and a second configuration when heated above the predetermined temperature transition range. The method further includes cooling the support member prior to inserting the annuloplasty ring into the annulus of the cardiac valve in order to place the support in the first configuration.

In accordance with another aspect of the inventive method, the support member is heated above the predetermined temperature transition range so that the support member changes into the second configuration.

In accordance with another aspect of the inventive method, heating the support member is done following the expansion of the support member with the balloon. The heating process contracts the annuloplasty ring and thereby restricts the valve annulus to support the valve annulus and correct valvular insufficiency.

In accordance with another aspect of the inventive method, the step of heating is accomplished by exposing the support member to body temperature.

In accordance with another aspect of the inventive method, the balloon and annuloplasty ring are inserted into the atrial chamber percutaneously via an intravascular catheter.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF EMBODIMENTS

Figure 1:
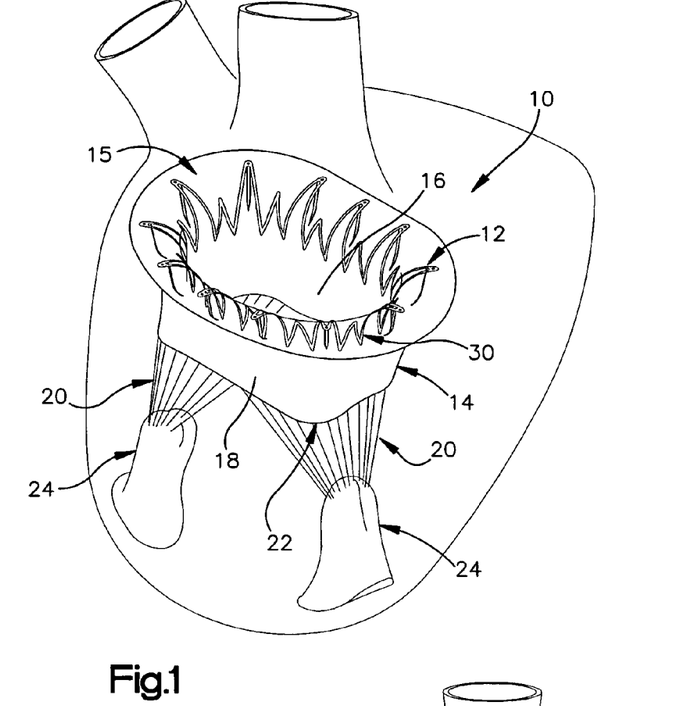
FIG. 1 is a schematic perspective view of a heart implanted with an annuloplasty ring for repairing a cardiac valve in accordance with the present invention.

The present invention relates to an apparatus and methods for repair of a cardiac valve. As representative of the present invention, FIG. 1 illustrates an apparatus 10 that includes an annuloplasty ring 12 for repairing a dysfunctional cardiac valve, such as a mitral valve 14. It should be understood, however, that the apparatus 10 disclosed herein could be used to repair not only a mitral valve, but also other cardiac valves and, in particular, a tricuspid valve.

Figure 2:
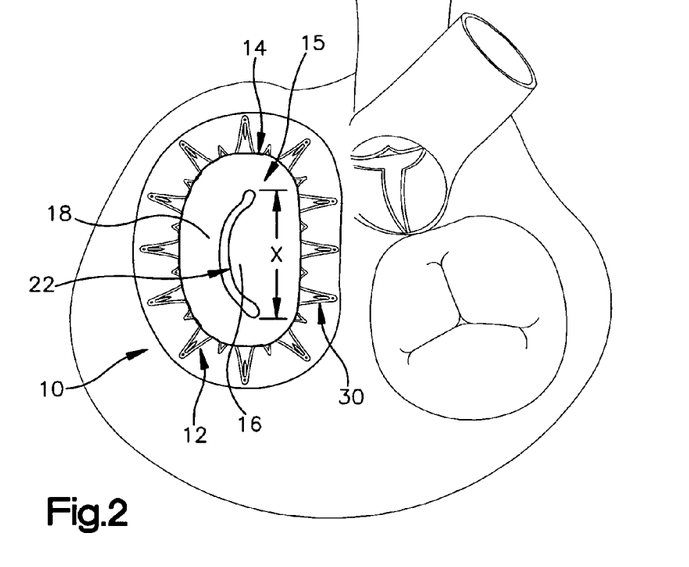
FIG. 2 is a schematic plan view of the heart and the annuloplasty ring shown in FIG. 1.

The mitral valve 14 is located between the left atrium and the left ventricle and functions to prevent the backflow of blood from the left ventricle into the left atrium during contraction. As best seen in FIG. 2, the mitral valve 14 has a D-shaped annulus 15 that defines the opening between the left atrium and the left ventricle. The mitral valve 14 is formed by two leaflets; namely, the anterior leaflet 16 and the posterior leaflet 18. The anterior leaflet 16 extends along the generally planar base of the D-shaped valve annulus 15 between two fibrous trigones (not shown). It is desirable to maintain the distance X (FIG. 2) between the two trigones after the valve repair procedure is completed. The posterior leaflet 18 extends arcuately around the curved portion of the D-shaped annulus 15 of the mitral valve 14. Chordae tendineae 20 (FIG. 1) extend between the free edges 22 of both leaflets 16 and 18 to the papillary muscles 24 in the left ventricle.

The annuloplasty ring 12 for repairing the dysfunctional mitral valve 14 comprises an expandable support member 30 that resembles a complete stent. The annuloplasty ring 12 described herein has an annular configuration that mimics the D-shape of the native annulus 15, but it will be understood by those skilled in the art that the annuloplasty ring could be a partial ring and thus have a C-shape, a U-shape, or another suitable configuration. The support member 30 is both flexible and resilient, and, as discussed in more detail below, is made of a shape memory material such as Nitinol. Other suitable medical grade metals or plastics having shape memory characteristics can also be used for the support member 30. The flexible and expandable properties of the support member 30 allow it to conform to the three-dimensional shape of the native valve annulus 14.

Figure 3:
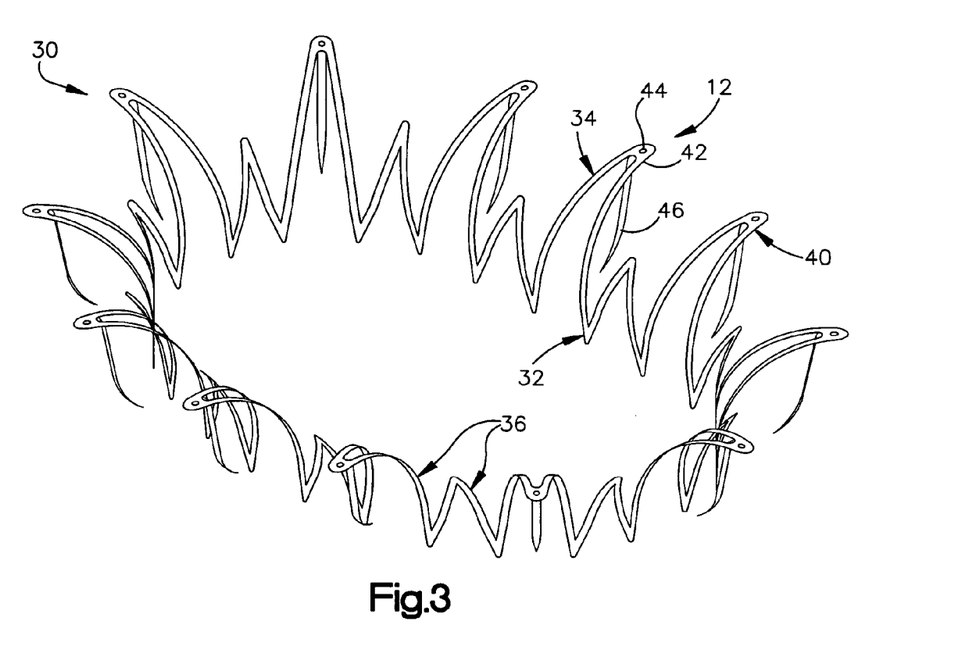
FIG. 3 is a perspective view of the annuloplasty ring of FIG. 1 illustrating the ring in a fully deployed condition.
Figure 6:
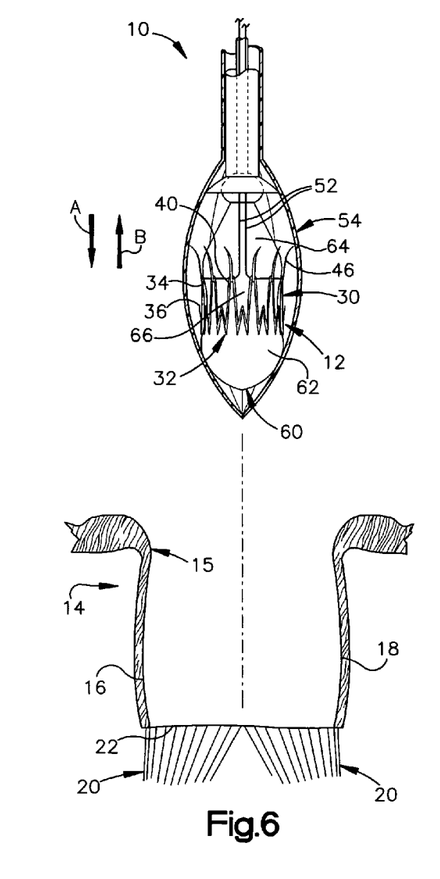
FIG. 6 is a side view, partly in section, of an apparatus for repairing a cardiac valve comprising the annuloplasty ring of FIG. 3, the apparatus being shown at an initial stage of delivery into an atrial chamber.

The support member 30 comprises a continuous series of W-shaped segments, although it is contemplated that other geometries could be used. The lower, as viewed in FIG. 3, tips of the W-shaped segments form a distal end portion 32 of the support member 30 and the elongated upper tips of the W-shaped segments form a proximal end portion 34 of the support member. For purposes of this disclosure, the term "proximal" means on the inflow or upstream side of the annuloplasty ring 12 and "distal" means on the outflow or downstream side of the annuloplasty ring. Thus, the distal end portion 32 of the support member 30 is the leading edge of the support member when the annuloplasty ring 12 is inserted into the body. Further, as illustrated in FIG. 6, the letter A indicates the distal direction and the letter B indicates the proximal direction.

Referring again to FIG. 3, a main body portion 36 of the support member 30 is defined between the distal and proximal end portions 32 and 34. The main body portion 36 has a concave cross-sectional shape for conforming to the convex shape of the valve annulus 15. It is contemplated that the pattern of the support member 30 and/or the thickness of the support member in the main body portion 36 may be altered along the inter-trigonal distance X in order to maintain this distance and ensure more retraction along the posterior leaflet 18.

The proximal end portion 34 of the support member 30 comprises a plurality of wing members 40 that resemble arches and which extend integrally from the main body portion 36 generally in the proximal direction B. The wing members 40 also have a concave cross-sectional shape for conforming to the convex shape of the valve annulus 15. As is shown in FIGS. 5-10, the main body portion 36 and the wing members 40 are resiliently bendable from their concave cross-sectional shapes into flatter cross-sectional shapes for delivery and placement of the annuloplasty ring 12.

Each wing member 40 of the support member 30 has a tip portion 42 (FIG. 3) that includes an aperture 44 for receiving a wire. Further, the tip portion 42 of each wing member 40 includes at least one hook member 46 for embedding into a cardiac wall to secure the annuloplasty ring 12 in the annulus 15 of the mitral valve 14. The hook members 46 project outward from the wing members 40 and have sharp pointed ends. It is contemplated that the pointed ends of the hook members 46 could include one or more barbs (not shown), similar to the barbs used in fishing hooks, to prevent pull-out of the hook members once they are embedded in the valve annulus 15.

As mentioned above, the support member 30 is made from a shape memory material, such as Nitinol, that is responsive to changes in temperature above and below a predetermined temperature transition range of 75-95 degrees Fahrenheit, although it should be understood that other temperature transition ranges could be used. The support member 30 has a first configuration when its temperature is below the predetermined temperature transition range and a second configuration when heated above the predetermined temperature transition range. In accordance with one aspect of the invention, the annuloplasty ring 12 is inserted into the annulus 15 of the mitral valve 14 in the first configuration, which is an expanded condition, and is thereafter heated above the predetermined temperature transition range to change the support member 30 into the second configuration, which is a contracted condition that is the desired pre-shape memorized by the material.

Figure 4:
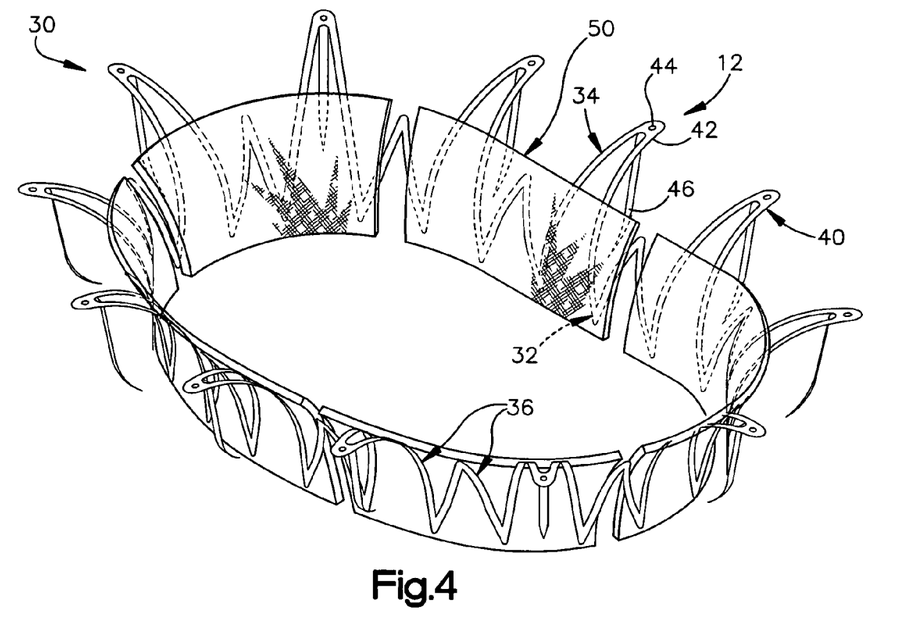
FIG. 4 is a perspective view similar to FIG. 3 illustrating an alternative construction for the annuloplasty ring.
Figure 5:
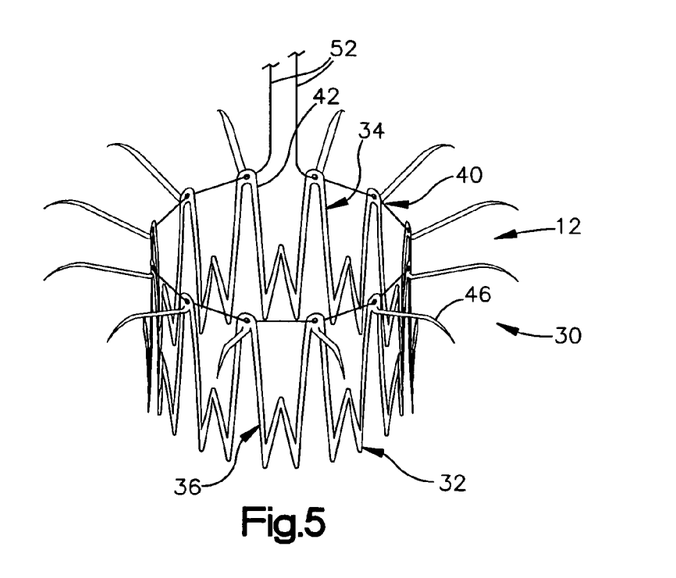
FIG. 5 is a perspective view of the annuloplasty ring of FIG. 3 with the ring being shown in a radially collapsed condition for delivery (prior to expansion by a balloon)

FIG. 4 illustrates the annuloplasty ring 12 with a layer 50 of biocompatible material covering sections of the distal end portion 32 and the main body portion 36 of the support member 30. The layer 50 of biocompatible material may be a synthetic such as Dacron®, woven velour, polyurethane, PTFE, or heparin-coated fabric. Alternatively, the layer 50 may be a biological material such as bovine or equine pericardium, a homograft, patient graft, or a cell-seeded tissue. The layer 50 can cover either the inside surface of the support member 30, the outside surface of the support member, or can be wrapped around both the inside and outside surfaces. The layer 50 may be attached around the entire circumference of the support member 30 or, alternatively, may be attached in sections as shown in FIG. 4 to allow the support member to more easily expand and contract.

The apparatus 10 further comprises a releasable constraining wire 52 (FIG. 5) for temporarily holding the wing members 46 in the flatter cross-sectional shape shown in FIGS. 5-10 during delivery and placement of the annuloplasty ring 12. The constraining wire 52 can be made from a variety of different materials including metals, polymers, synthetics, fabrics, and biological tissues. As illustrated in FIGS. 5 and 7-10, the hook members 46 extend generally radially when the wing members 40 are being held in the flatter cross-sectional shape by the constraining wire 52. However, as shown in FIG. 6, the hook members 46 are resiliently bendable to extend proximally inside a delivery capsule 54 during delivery of the annuloplasty ring 12 into the valve annulus 15. It should be understood that the delivery capsule 54 could have a variety of configurations, including a sleeve or sheath.

The apparatus 10 further comprises an inflatable balloon 60 (FIG. 6) for expanding the annuloplasty ring 12 into full and complete contact with the annulus 15 of the cardiac valve 14. The balloon 60 has an hourglass shape defined by first and second bulb sections 62 and 64 connected by a center section 66. Each of these sections 62, 64 and 66 may have a D-shaped diameter (or other shaped diameter) to match the D-shaped diameter of the valve 14 and the annuloplasty ring 12. The center section 66 of the balloon 60 has a smaller diameter than the bulb sections 62 and 64. The first and second bulb sections 62 and 64 and the center section 66 may be inflated together or separately. Further, the sections 62, 64 and 66 may have multiple chambers to accommodate multiple fluids (i.e., an inflation fluid and a cooling fluid).

To repair the mitral valve 14 with the apparatus 10 using a percutaneous (or intravascular) approach, the annuloplasty ring 12 is properly sized for the mitral valve by the surgical team using fluoroscopic and/or echocardiographic data. The annuloplasty ring 12 may be cooled using a cryogenic source or other suitable means to place the support member 30 in its first configuration. The annuloplasty ring 12 is then positioned about the center section 66 of the balloon 60. It is contemplated that the annuloplasty ring 12 could alternatively, or as a supplement, be cooled by infusing the balloon with a cooling fluid or other medium. The constraining wire 52 is pulled tight, which results in the wing members 40 bending radially inward from their convex cross-sectional shape to the flatter cross-sectional shape of FIG. 6. The delivery capsule 54 is then placed over the balloon 60 and the annuloplasty ring 12. Inside the capsule 54, the hook members 46 are bent upward in the proximal direction B. The apparatus 10 is then loaded into an 16 to 22 French catheter (not shown) in a known manner.

The apparatus 10 is introduced into the right jugular vein using a known percutaneous technique called the Seldinger technique and is advanced through the superior vena cava to approach the right atrium. The catheter is then passed through the interatrial septum to reach the left atrium. Inside the left atrium, the apparatus 10 is positioned just above the mitral valve 14 as is shown in FIG. 6.

Figure 7:
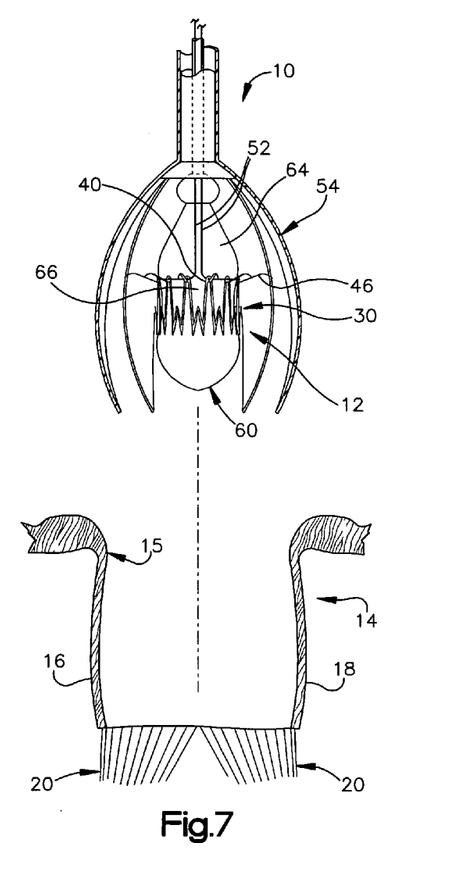
FIG. 7 is a side view similar to FIG. 6 illustrating the apparatus at a subsequent stage of delivery.
Figure 8:
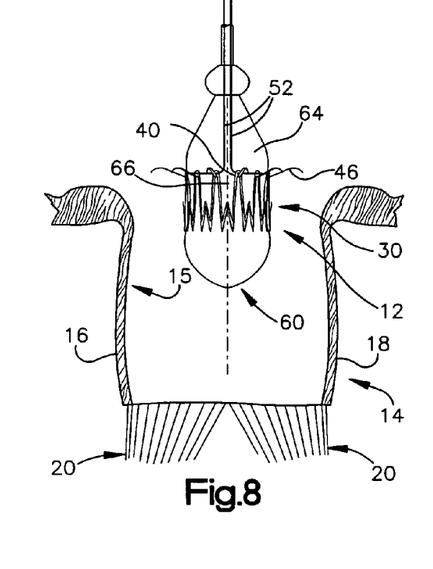
FIG. 8 is a side view similar to FIG. 7 illustrating the apparatus at another subsequent stage of delivery.

Next, the delivery capsule 54 is opened, which exposes the balloon 60 and the annuloplasty ring 12 and also allows the hook members 46 to spring back to the position illustrated in FIG. 7. The balloon 60 is then advanced distally into the annulus 15 of the mitral valve 14 until the center section 66 of the balloon 60 (where the annuloplasty ring 12 is positioned) is at the level of the annulus, as shown in FIG. 8.

Figure 9:
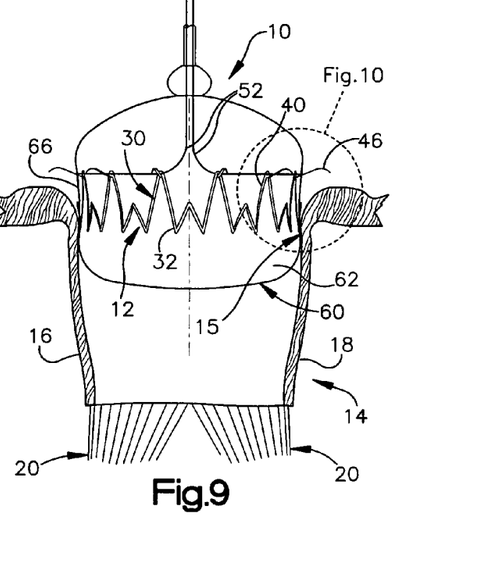
FIG. 9 is a side view similar to FIG. 8 illustrating the annuloplasty ring being deployed in the valve annulus by expansion of a balloon.
Figure 10:
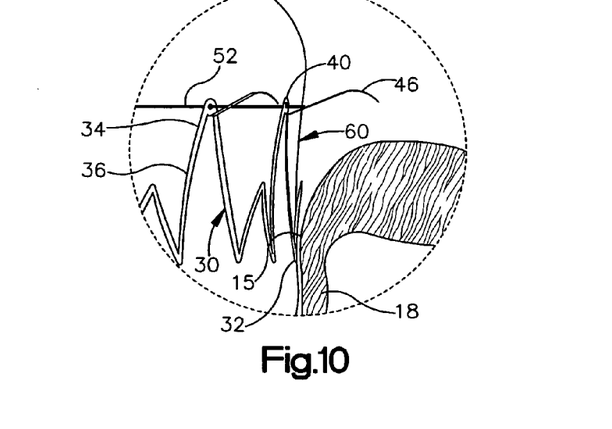
FIG. 10 is an enlarged view of a portion of FIG. 9.

Next, the balloon 60 is inflated to radially expand the annuloplasty ring 12 into full and complete engagement with the valve annulus 15. When the balloon 60 is inflating, the first bulb 62 pushes the valve leaflets 16 and 18 back to protect the leaflets during expansion of the support member 30. The constraining wire 52 is loosed slightly to compensate for the growing diameter of the expanding balloon 60, but the wire is not completely released. This keeps the wing members 40 held against the balloon 60 for the time being, and also keeps the hook members 46 pointed above the level of the valve annulus 15. The balloon 60 is inflated to the point where the ring 12 is over-expanded in order to ensure full and complete engagement with diseased/dilated annulus 15. As is illustrated in FIGS. 9 and 10, this full annular engagement of the distal end portion 32 of the support member 30 ensures that the annuloplasty ring 12 seats against the inside of the valve annulus 15 and forms a point of fixation for the annuloplasty ring.

Figure 11:
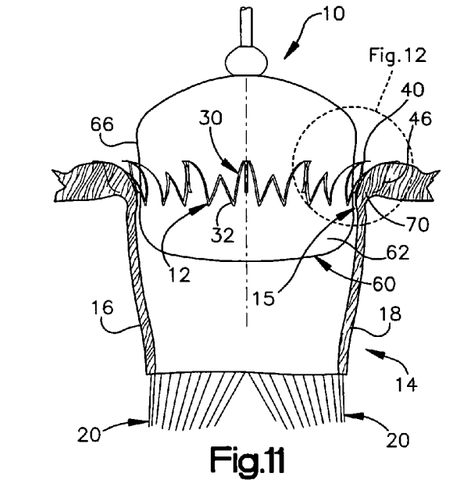
FIG. 11 is a side view similar to FIG. 9 illustrating a further step in the deployment of the annuloplasty ring.
Figure 12:
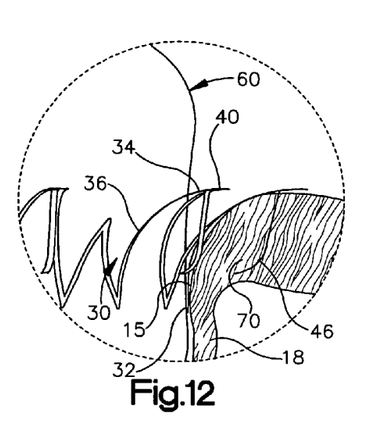
FIG. 12 is an enlarged view of a portion of FIG. 11.

The constraining wire 52 is then released, which allows the main body portion 36 and the wing members 40 of the support member 30 to spring back to their convex shape as shown in FIG. 11. As the wing members 40 bend radially outward, the hook members 46 swing downward in the distal direction A and embed into the cardiac wall 70 and the valve annulus 15. The embedded hook members 46 thus extend distally from the wing members 40 into the cardiac wall 70 to provide the primary point of fixation for the annuloplasty ring 12. As shown in FIG. 12, the convex shape of the support member 30 conforms to the concave shape of the valve annulus 15 and the annuloplasty ring 12 becomes clamped in the annulus between the distal end portion 32 of the support member and the distally extending hook members 46.

Figure 13:
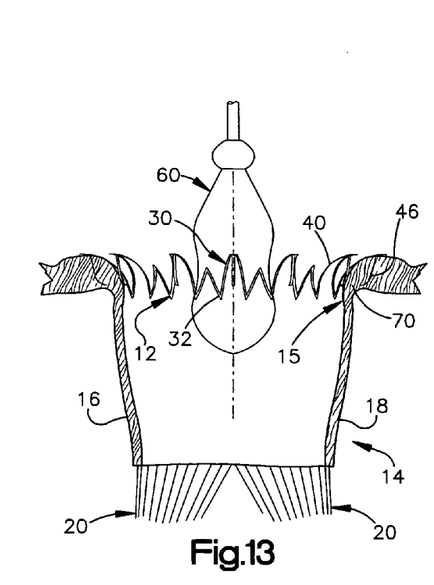
FIG. 13 is a side view similar to FIG. 11 illustrating the annuloplasty ring implanted in the valve annulus with the balloon deflated.
Figure 14:
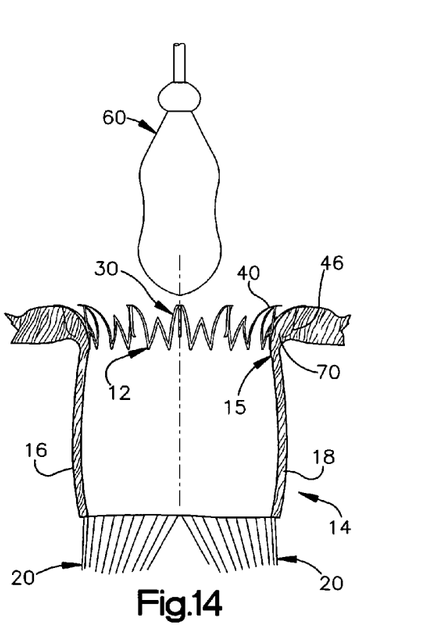
FIG. 14 is a side view similar to FIG. 13 illustrating the constricting effect that the shape memory material of the annuloplasty ring has on the valve annulus.

As shown in FIGS. 13 and 14, the balloon 60 is then deflated and moved out of the valve annulus 15. FIG. 14 also illustrates the final step in the process whereby exposure of the support member 30 to body temperature over time raises the temperature above the transition range. It is contemplated that the temperature of the support member 30 could also be elevated by infusing the balloon 60 with warm saline. Raising the temperature of the support member 30 above the transition range causes the annuloplasty ring 12 to contract, which reduces the size of the opening of the valve annulus 15 to a predetermined size and shape defined by the second configuration for the support member 30. It should be noted that the constriction of the annuloplasty ring 12 to the predetermined size reduces the posterior portion of the annulus 15 but maintains the desired inter-trigonal distance X as another mechanism of fixation.

The constriction of the annuloplasty ring 12 due to the shape memory material of the support member 30 thus reestablishes the size of the valve annulus 15 to normal. The flexibility of the support member 30 allows the annuloplasty ring 12 to follow the native shape and contour of the valve annulus, yet provide structural support for the annulus which improves the coaptation of the native leaflets 16 and 18 and restores normal valve function.

Before the balloon 60 and the constraining wire 52 are completely withdrawn, the competency of the remodeled valve 14 can be tested by echocardiogram. If necessary, the annuloplasty ring 12 can be re-positioned by tightening the constraining wire 52 to pull the wing members 40 and the hook members 46 upward and out of the cardiac wall 70 and the annulus 15, and then re-inflating the balloon 60 to re-acquire the annuloplasty ring. If the echocardiogram shows the valve repair to be successful, then the constraining wire 52 is pulled out of the apertures 44 in the hook members 46 and the rest of the apparatus 10, including the balloon 60, is removed from the atrial chamber.

The present invention thus allows for the annuloplasty ring 12 to be delivered in a cardiac catheterization laboratory with a percutaneous approach under local anesthesia using fluoroscopic as well as echocardiographic guidance, thereby avoiding general anesthesia and highly invasive open heart surgery techniques. This approach offers tremendous advantages for high risk patients with severe valvular regurgitation. It should be understood, however, that the present invention contemplates various other approaches, including standard open heart surgeries as well as minimally invasive surgical techniques. Because the present invention omits stitching of the annuloplasty ring 12 in the valve annulus 15, surgical time is reduced regardless of whether an open or percutaneous approach is used.

The technique for implanting the annuloplasty ring 12 in the tricuspid valve follows the same steps described above for the mitral valve 14, except that all of the delivery and implantation steps for a tricuspid annuloplasty ring take place inside the right atrium and on a dilated native tricuspid valve. The annuloplasty ring 12 disclosed herein is capable of achieving an adjustable restriction in a deeper portion of the posterior leaflet segment and in a small portion of the adjacent anterior leaflet. The septal leaflet segment is not usually required to be shortened, so the tricuspid valve annuloplasty ring improves leaflet coaptation and valve function by restriction of the anterior and posterior portions of the native valve tricuspid annulus.

From the above description of the invention, those skilled in the art will perceive improvements, changes and modifications. For example, it is contemplated that, in addition to the balloon-based apparatus disclosed herein, a mechanical-based apparatus could be used to deliver and deploy the annuloplasty ring described herein. Such improvements, changes and modifications within the skill of the art are intended to be covered by the appended claims.

Having described the invention, we claim:

1. An annuloplasty ring for repairing a cardiac valve, said annuloplasty ring comprising:
   an expandable support member having oppositely disposed proximal and distal end portions and a main body portion between said end portions, said proximal end portion of said support member comprising a plurality of wing members that extend from said main body portion; and
   each of said wing members including at least one fixation hook member, said at least one fixation hook member extending distally between said wing member and a location laterally adjacent said main body portion when said at least one fixation hook member is embedded into a cardiac wall and the annulus of the cardiac valve to secure said annuloplasty ring in the annulus.

2. The annuloplasty ring of claim 1 wherein said main body portion has a concave cross-sectional shape for conforming to the convex shape of the valve annulus.

3. The annuloplasty ring of claim 2 wherein each of said wing members has a concave cross-sectional shape for conforming to the convex shape of the valve annulus.

4. The annuloplasty ring of claim 3 wherein said main body portion and said wing members are resiliently bendable from said concave cross-sectional shapes into flatter cross-sectional shapes for delivery and placement of said annuloplasty ring.

5. The annuloplasty ring of claim 4 further comprising a constraining wire for temporarily holding said wing members in said flatter cross-sectional shape, said hook members extending generally radially when said wing members are being held in said flatter cross-sectional shape by said constraining wire.

6. The annuloplasty ring of claim 5 wherein said hook members are resiliently bendable to extend proximally inside a delivery capsule during delivery of said annuloplasty ring into the valve annulus.

7. The annuloplasty ring of claim 1 further comprising a layer of biocompatible material covering at least a portion of said distal end portion and said main body portion of said support member.

8. The annuloplasty ring of claim 1 wherein said support member is made from a shape memory material that is responsive to changes in temperature above and below a predetermined temperature transition range, said support member having a first configuration when the temperature is below said predetermined temperature transition range, said support member having a second configuration when heated above said predetermined temperature transition range.

9. The annuloplasty ring of claim 8 wherein said support member is insertable into the annulus of the cardiac valve in said first configuration and is thereafter heatable above said predetermined temperature transition range to change said support member into said second configuration, wherein movement of said support member into said second configuration causes a reduction in size of the opening defined by the valve annulus.

10. The annuloplasty ring of claim 1 wherein said support member is expandable by an inflatable balloon so that said annuloplasty ring engages the annulus of the cardiac valve.

11. An apparatus for repairing a cardiac valve, said apparatus comprising:
an annuloplasty ring including an expandable support member having oppositely disposed proximal and distal end portions and a main body portion between said end portions, said proximal end portion of said support member comprising a plurality of wing members that extend from said main body portion;
each of said wing members including at least one fixation hook member, said at least one fixation hook member extending distally between said wing member and a location laterally adjacent said main body portion when said at least one fixation hook member is embedded into a cardiac wall and the valve annulus to secure said annuloplasty ring in the annulus of the cardiac valve; and
an inflatable balloon for expanding said support member so that said annuloplasty ring engages the annulus of the cardiac valve.

12. The apparatus of claim 11 wherein said main body portion has a concave cross-sectional shape for conforming to the convex shape of the valve annulus.

13. The apparatus of claim 12 wherein each of said wing members has a concave cross-sectional shape for conforming to the convex shape of the valve annulus.

14. The apparatus of claim 13 where said main body portion and said wing members are resiliently bendable from said concave cross-sectional shapes into flatter cross-sectional shapes for delivery and placement of said annuloplasty ring.

15. The apparatus of claim 14 further comprising a constraining wire for temporarily holding said wing members in said flatter cross-sectional shape, said hook members extending generally radially when said wing members are being held in said flatter cross-sectional shape by said constraining wire.

16. The apparatus of claim 15 wherein said hook members are resiliently bendable to extend proximally inside a delivery capsule during delivery of said annuloplasty ring into the valve annulus.

17. The apparatus of claim 11 further comprising a layer of biocompatible material covering at least a portion of said distal end portion and said main body portion of said support member.

18. The apparatus of claim 11 wherein said support member is made from a shape memory material that is responsive to changes in temperature above and below a predetermined temperature transition range, said support member having a first configuration when the temperature is below said predetermined temperature transition range, said support member having a second configuration when heated above said predetermined temperature transition range.

19. The apparatus of claim 18 wherein said support member is insertable into the annulus of the cardiac valve in said first configuration and is thereafter heatable above said predetermined temperature transition range to change said support member into said second configuration, wherein movement of said support member into said second configuration causes a reduction in size of the opening defined by the valve annulus.

20. The apparatus of claim 11 wherein said balloon has an hourglass shape defined by first and second bulb sections connected by a center section having a smaller diameter than said bulb sections, said annuloplasty ring being positioned about said center section.

* * * * *